United States Patent [19]

Stanko

[11] Patent Number: 4,874,790
[45] Date of Patent: Oct. 17, 1989

[54] METHOD FOR IMPROVING THE GLUCOSE METABOLISM OF AN ANIMAL HAVING DIABETIC TENDENCIES

[75] Inventor: Ronald T. Stanko, Pittsburgh, Pa.

[73] Assignee: Montefiore Hospital Association of Western Pennsylvania, Pittsburgh, Pa.

[21] Appl. No.: 232,119

[22] Filed: Aug. 15, 1988

[51] Int. Cl.$^4$ .............................................. A61K 31/19
[52] U.S. Cl. ..................................... 514/557; 514/866
[58] Field of Search ................................. 514/557, 866

[56] References Cited

U.S. PATENT DOCUMENTS 4,351,835 9/1982 Stanko .............................. 514/557 X

*Primary Examiner*—Frederick E. Waddell
*Attorney, Agent, or Firm*—Harry B. Keck

[57] ABSTRACT

A method for treating animals having diabetic tendencies to improve the glucose metabolism of the animal by oral administration of therapeutically effective amounts of pyruvate and dihydroxyacetone. The treatment lowers Glucose Tolerance Test Values and lowers Fasting Blood Glucose Test values.

9 Claims, No Drawings

METHOD FOR IMPROVING THE GLUCOSE METABOLISM OF AN ANIMAL HAVING DIABETIC TENDENCIES

BACKGROUND OF THE INVENTION

1. Field of the Invention

This invention concerns oral administration of pyruvate and dihydoxyacetone to animals having diabetic tendencies to improve the glucose metalbolism of said animals.

2. Description of the Prior Art

Pyruvate and dihydroxyacetone and mixtures of pyruvate and dihydroxyacetone have been described for a number of beneficial results:

U.S. Pat. No. 4,158,057 describes oral administration of pyruvate and dihydroxyacetone to prevent excessive accumulation of fatty deposits in a mammal liver due to ethanol ingestion.

U.S. Pat. No. 4,351,835 describes oral administration of pyruvate and dihydroxyacetone to reduce an expected weight gain from a given diet or to induce a weight loss in a mammal. The patent also describes oral administration of pyruvate and dihydroxyacetone to athletes prior to strenuous athletic events to increase endurance and/or performance.

U.S. Pat. No. 4,415,575 describes oral administration of pyruvate and dihydroxyacetone to increase the body protein concentration in a mammal.

U.S. Pat. No. 4,458,937 describes oral administration of pyruvate to a mammal to induce a weight loss or reduce an expected weight gain from a given diet.

U.S. Pat. No. 4,645,764 descrieb oral administration to a living being of pyruvate and dihydroxyacetone to induce a weight loss or to reduce an expected weight gain from a given diet and for inhibiting body fat while increasing body protein concentration.

Copending U.S. application Ser. No. 901,402, now U.S. Pat. No. 4,812,478, describes oral administration of dihydroxyacetone to an animal to induce a weight loss or to reduce an expected weight gain from a given diet.

Copending patent application Ser. No. 232,118, filed on even date herewith, describes the use of pyruvate and dihydoxyacetone for increasing the glucose uptake in the muscles of an animal.

These described results of oral administration of pyruvate and/or dihydroxyacetone are of great interest for medical patients who ingest ethanol; medical patients having fatty liver deposits or tendencies toward fatty liver deposits; medical patients who are obese or have a tendency toward obesity; normalsubjects desiring to lose body weight or to retard body weight increase; normal patients, particularly athletes, who desire to increase endurance.

STATEMENT OF THE PRESENT INVENTION

According to the present invention I have discovered that the glucose metabolism is improved in an animal having diabetic tendencies when the animal has received oral administration of pyruvate and dihydroxyacetone.

DESCRIPTION OF THE PREFERRED EMBODIMENTS

Glucose Tolerance Tests

A common diabetes indicator is a Glucose Tolerance test. In the Glucose Tolerance test, the subject receives orally 75 grams of pur glucose. The subject's blood glucose is measured immediately and thereafter for about 3 hours. Glucose values above about 200 in sixty minutes indicate likelihood of diabetes conditions in the subject. One diabetic subject, A.B., received a Glucose Tolerance test under two circumstances. Firstly, with no prior medication, and secondly, following medication of 52 grams per day of a mixture of 1 part by weight pyruvate and 1 part by weight dihydroxyacetone orally administered for seven days. The subject was on a 1500 calories per day maintenance diet. The dosage of 26 grams pyruvate and 26 grams dihydroxyacetone corresponds to 15% of the daily calories.

| Results of Glucose Tolerance Tests - A.B. | | |
|---|---|---|
| Times (Minutes) | Without Medication | With Medication |
| 0 | 104 | 96 |
| 30 | 155 | 134 |
| 60 | 213 | 193 |
| 120 | 245 | 237 |
| 180 | 204 | 183 |

The described treatment results in significantly lower glucose values initially and throughout the three-hour evaluation. The 60-minute value for the patient with medication was less than the threshold level of 200.

Fasting Blood Glucose Tests

Another diabetes test is a Fasting Blood Glucose test in which the subject refrains from eating overnight and the glucose test is administered in the morning. One diabetic subject, D.C., received the Fasting Blood Glucose Tests under two circumstances. Firstly with no medication. Secondly, following medication of 52 grams daily for seven days, orally administered, of 1 part pyruvate by weight dihydroxyacetone and 1 part by weight pyruvate. The subject was on a 1500 calories per day maintenance diet. The dosage of 26 grams pyruvate and 26 grams dihydroxyacetone corresponds to 15% of the daily calories. The Fasting Blood Glucose Values are set forth:

| | C.D. Without Medication | C.D. With Medication |
|---|---|---|
| Fasting Blood Glucose Value | 312 | 206 |

The mixture of pyruvate and dihydoxyacetone reduced the diabetic subject's Fasting Blood Blucose Value significantly.

I claim:

1. A method for treating an animal having diabetic tendencies to improve its Glucose Tolerance, as measured by a Glucose Tolerance Test, which comprises administering orally to the animal a therapeutically effective amount of pyruvate and dihydroxyacetone prior to administering a Glucose Tolerance Test whereby the animal exhibits lower values in the said Glucose Tolerance Test than exhibited in the absence of said amount.

2. A method for treating an animal having diabetic tendencies to lower its Fasting Blood Glucose Values, as measured by a Fasting Blood Glucose Tolerance Test, which comprises administering orally to the animal a therapeutically effective amount of pyruvate and dihydoxyacetone prior to administering a Fasting Blood Glucose Tolerance Test whereby the animal ehixibts a lower value in the said Fasting Blood Glucose Tolerance Test than exhibited in the absence of said amount.

3. A method for improving the glucose metabolism of an animal having diabetic tendencies which comprises administering orally to the animal a therapeutically effective amount of pyruvate and dihydroxyacetone.

4. The method of claim 1 wherein the ratio of dihydroxyacetone to pyruvate is 1:1.

5. The method of claim 2 wherein the ratio of dihydroxyacetone to pyruvate is 1:1.

6. The method of claim 3 wherein the ratio of dihydroxyacetone to pyruvate is 1:1.

7. The method of claim 1 wherien the said therapeutically effective amount of pyruvate and dihydoxyacetone is administered for at least seven days.

8. The method of claim 2 wherein the said therapeutically effective amount of pyruvate and dihydroxyacetone is administered for at least seven days.

9. The method of claim 3 wherein the said therapeutically effective amount of pyruvate and dihydroxyacetone is administered for at least seven days.

* * * * *